United States Patent
Junio (10) Patent No.: US 12,042,171 B2
(45) Date of Patent: Jul. 23, 2024

(54) SYSTEMS AND METHODS FOR SURGICAL PORT POSITIONING

(71) Applicant: Mazor Robotics Ltd., Caesarea (IL)

(72) Inventor: Dany Junio, Tel Aviv-Jaffa (IL)

(73) Assignee: Mazor Robotics Ltd., Caesarea (IL)

( * ) Notice: Subject to any disclaimer, the term of this patent is extended or adjusted under 35 U.S.C. 154(b) by 322 days.

(21) Appl. No.: 17/475,177

(22) Filed: Sep. 14, 2021

(65) Prior Publication Data
US 2022/0192701 A1   Jun. 23, 2022

Related U.S. Application Data

(60) Provisional application No. 63/128,560, filed on Dec. 21, 2020.

(51) Int. Cl.
| | | |
|---|---|---|
| A61B 17/34 | (2006.01) | |
| A61B 34/00 | (2016.01) | |
| A61B 34/10 | (2016.01) | |
| A61B 34/30 | (2016.01) | |
| A61B 1/00 | (2006.01) | |
| A61B 17/00 | (2006.01) | |
| A61B 90/00 | (2016.01) | |

(52) U.S. Cl.
CPC .......... *A61B 17/3423* (2013.01); *A61B 34/30* (2016.02); *A61B 34/76* (2016.02); *A61B 1/00154* (2013.01); *A61B 2017/00119* (2013.01); *A61B 2017/00699* (2013.01); *A61B 2034/107* (2016.02); *A61B 2034/302* (2016.02); *A61B 2090/064* (2016.02)

(58) Field of Classification Search
CPC ................ A61B 17/3423; A61B 34/76; A61B 2017/00119; A61B 2017/00699; A61B 34/30; A61B 1/00154; A61B 2034/107; A61B 2034/302; A61B 2090/064
See application file for complete search history.

(56) References Cited

U.S. PATENT DOCUMENTS

| | | | |
|---|---|---|---|
| 9,936,972 B2 * | 4/2018 | Blohm | A61B 17/3476 |
| 10,022,194 B2 | 7/2018 | Prisco | |
| 10,258,419 B2 * | 4/2019 | Auld | A61B 34/30 |
| 10,426,558 B2 * | 10/2019 | Scholan | H10B 41/27 |

(Continued)

FOREIGN PATENT DOCUMENTS

| | | |
|---|---|---|
| EP | 2480145 | 12/2017 |
| EP | 3468498 | 4/2019 |

(Continued)

OTHER PUBLICATIONS

Extended Search Report for European Patent Application No. 21215100.5, dated May 31, 2022, 11 pages.

*Primary Examiner* — Ryan J. Severson
(74) *Attorney, Agent, or Firm* — Sheridan Ross P.C.

(57) ABSTRACT

A method for robot-assisted minimally invasive surgery involves calculating, based on a surgical plan, an insertion vector for an MIS port; causing a robotic arm to hold the MIS port in a pose that corresponds to the insertion vector; detecting, with a sensor on the robotic arm, a force applied to the robotic arm via the MIS port; maintaining the MIS port in the pose when the detected force is lower than a predetermined threshold; and generating an alert when the detected force exceeds the predetermined threshold.

20 Claims, 3 Drawing Sheets

(56) References Cited

U.S. PATENT DOCUMENTS

| | | | |
|---|---|---|---|
| 10,512,514 B2 | 12/2019 | Nowlin et al. | |
| 10,639,108 B2* | 5/2020 | Romo | A61B 1/00135 |
| 10,661,453 B2 | 5/2020 | Koenig et al. | |
| 10,687,904 B2* | 6/2020 | Harris | A61B 17/3421 |
| 10,849,700 B2* | 12/2020 | Kopp | A61B 34/35 |
| 11,039,894 B2* | 6/2021 | Anderson | A61B 90/39 |
| 11,076,925 B2* | 8/2021 | DiMaio | A61B 46/10 |
| 11,147,642 B2* | 10/2021 | Yeung | A61B 34/71 |
| 11,154,183 B2* | 10/2021 | Yeung | A61B 17/3421 |
| 11,166,770 B2* | 11/2021 | DiMaio | A61B 34/00 |
| 11,280,690 B2* | 3/2022 | Lin | A61B 1/00006 |
| 2009/0171374 A1* | 7/2009 | Omori | A61B 34/71 |
| | | | 606/130 |
| 2015/0297299 A1 | 10/2015 | Yeung et al. | |
| 2016/0128781 A1 | 5/2016 | Blohm et al. | |
| 2016/0166342 A1* | 6/2016 | Prisco | B25J 9/1045 |
| | | | 606/130 |
| 2017/0086932 A1 | 3/2017 | Auld et al. | |
| 2017/0119481 A1* | 5/2017 | Romo | A61B 1/00096 |
| 2017/0143435 A1* | 5/2017 | Scholan | A61B 34/30 |
| 2018/0042687 A1* | 2/2018 | Nowlin | A61B 34/35 |
| 2018/0049824 A1 | 2/2018 | Harris et al. | |
| 2018/0079090 A1* | 3/2018 | Koenig | G01L 3/14 |
| 2018/0250084 A1 | 9/2018 | Kopp et al. | |
| 2018/0325614 A1 | 11/2018 | Yeung et al. | |
| 2019/0216555 A1 | 7/2019 | DiMaio et al. | |
| 2019/0231460 A1 | 8/2019 | DiMaio et al. | |
| 2019/0321115 A1* | 10/2019 | Anderson | A61B 17/3423 |
| 2020/0217733 A1 | 7/2020 | Lin et al. | |
| 2022/0192701 A1* | 6/2022 | Junio | A61B 34/76 |
| 2022/0241017 A1* | 8/2022 | Junio | A61B 34/32 |
| 2022/0241031 A1* | 8/2022 | Junio | A61B 34/10 |
| 2022/0257320 A1* | 8/2022 | Junio | A61B 34/30 |
| 2022/0270263 A1* | 8/2022 | Junio | G06T 7/11 |

FOREIGN PATENT DOCUMENTS

| | | |
|---|---|---|
| WO | WO 2019/136062 | 7/2019 |
| WO | WO 2020/131304 | 6/2020 |

* cited by examiner

SYSTEMS AND METHODS FOR SURGICAL PORT POSITIONING

CROSS REFERENCE TO RELATED APPLICATIONS

This application claims the benefit of U.S. Provisional Application No. 63/128,560, filed on Dec. 21, 2020, and entitled "Systems and Methods for Surgical Port Positioning", which application is incorporated herein by reference in its entirety.

FIELD

The present technology relates generally to robotic surgery and relates more particularly to robot-assisted or robotic surgery using a surgical port.

BACKGROUND

Minimally invasive surgery beneficially reduces patient trauma by minimizing the size of needed incisions. Surgical robots are useful during surgeries, and may operate autonomously (e.g., without any human input during operation), semi-autonomously (e.g., with some human input during operation), or non-autonomously (e.g., only as directed by human input). In some situations, use of multiple robotic arms during a surgery can enable more to be accomplished in a shorter period of time than with only one robotic arm.

SUMMARY

Example aspects of the present disclosure include:

A method for robot-assisted minimally invasive surgery, comprising: calculating, based on a surgical plan, an insertion vector for an MIS port; causing a robotic arm to hold the MIS port in a pose that corresponds to the insertion vector; detecting, with a sensor on the robotic arm, a force applied to the robotic arm via the MIS port; maintaining the MIS port in the pose when the detected force is lower than a predetermined threshold; and generating an alert when the detected force exceeds the predetermined threshold.

Any of the aspects herein, wherein maintaining the MIS port in the pose comprises causing the robotic arm to apply a responsive force to the MIS port, the responsive force based on the detected force.

Any of the aspects herein, wherein the robotic arm is a first robotic arm and the sensor is a first sensor, the method further comprising: causing a second robotic arm to carry out a surgical task via the MIS port based on the surgical plan.

Any of the aspects herein, wherein the sensor is a first sensor, the method further comprising: receiving, from a second sensor on the second robotic arm, information about an applied force exerted by the second robotic arm.

Any of the aspects herein, further comprising: controlling the first robotic arm based on the applied force to prevent movement of the MIS port.

Any of the aspects herein, further comprising: causing the second robotic arm to reduce the applied force when the applied force reaches the predetermined threshold.

Any of the aspects herein, wherein the insertion vector is a first insertion vector and the pose is a first pose, the method further comprising: calculating a second insertion vector based on the surgical plan; and causing the robotic arm to move the MIS port to a second pose that corresponds to the second insertion vector, the second pose different than the first pose.

Any of the aspects herein, wherein the pose is a first pose, the method further comprising: causing the robotic arm to move the MIS port to a second pose different than the first pose based on user input.

Any of the aspects herein, wherein the MIS port remains at least partially inside a patient during movement of the MIS port from the first pose to the second pose.

Any of the aspects herein, further comprising: causing the robotic arm to carry out a surgical task based on the surgical plan while holding the MIS port in the pose.

Any of the aspects herein, wherein the surgical plan describes a surgical procedure to be carried out on a patient, the method further comprising: registering a robotic coordinate system corresponding to the robotic arm to a patient coordinate system corresponding to the patient.

Any of the aspects herein, wherein the predetermined threshold is based on forces exerted on the MIS port as a result of breathing motion.

Any of the aspects herein, wherein the predetermined threshold corresponds to a maximum force expected during a surgical procedure involving the MIS port.

A system for use during minimally invasive surgery, comprising: a robotic arm; a sensor; at least one processor; and a memory storing instructions for execution by the at least one processor. The instructions, when executed, cause the at least one processor to: determine, based on a surgical plan for a patient, a pose for an MIS port; cause the robotic arm to hold the MIS port in the pose; receive, from the sensor, information about a force exerted on the robotic arm via the MIS port; maintain the MIS port in the pose when the force is lower than a predetermined threshold; and generate an alert when the force exceeds the predetermined threshold.

Any of the aspects herein, wherein the MIS port comprises the sensor.

Any of the aspects herein, wherein the robotic arm comprises the sensor.

Any of the aspects herein, wherein the robotic arm is a first robotic arm, the sensor is a first sensor, the system further comprises a second robotic arm comprising a second sensor, and the memory stores additional instructions for execution by the at least one processor that, when executed, further cause the at least one processor to: control the second robotic arm to carry out a surgical task via the MIS port.

Any of the aspects herein, wherein the memory stores additional instructions for execution by the at least one processor that, when executed, further cause the at least one processor to: receive, from the second sensor, information about an applied force exerted by the second robotic arm on the MIS port; and control the first robotic arm based on the information from the second sensor.

Any of the aspects herein, wherein the memory stores additional instructions for execution by the at least one processor that, when executed, further cause the at least one processor to: cause the robotic arm to carry out a surgical task via the MIS port while holding the MIS port in the pose.

Any of the aspects herein, wherein the memory stores additional instructions for execution by the at least one processor that, when executed, further cause the at least one processor to: move the MIS port to a new pose different than the pose.

Any of the aspects herein, wherein the alert comprises at least one of a visual alert, an audible alert, or a tactile alert.

Any of the aspects herein, wherein the determining comprises calculating an insertion vector based on the surgical plan.

Any of the aspects herein, wherein the predetermined threshold is based on a characteristic of the robotic arm.

Any of the aspects herein, wherein the surgical plan describes a spinal surgical procedure.

A system for providing robotic assistance during surgery, comprising: a robotic arm; at least one processor; and a memory storing instructions for execution by the at least one processor. The instructions, when executed, cause the at least one processor to: calculate, based on a surgical plan for a patient, pose for a surgical port; register a robotic coordinate space corresponding to the robotic arm to a patient coordinate space corresponding to the patient; cause the robotic arm to hold the surgical port in the pose; control the robotic arm to maintain the surgical port in the pose unless a force exerted on the surgical port exceeds a predetermined threshold; and when the force exceeds the predetermined threshold, generate an alert.

Any of the aspects herein, wherein the surgical port is an MIS port.

Any of the aspects herein, wherein the surgical port is an endoscopy port.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment. The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Minimally invasive surgery (MIS) may be carried out through a port that holds open a skin incision. Endoscopic surgery may be carried out through a port positioned within an opening to the body (e.g., a mouth, an anus). In both cases, one or more tools are passed through the surgical port (whether the MIS port or the endoscopy port) during the surgical procedure. The port may define a proper trajectory for the one or more tools, so as to guide the tools to a target anatomical element or volume.

A surgical port may be placed manually by a physician, whether with or without the assistance of a navigation system. During manual placement, the surgical port may be held by an arm having multiple lockable joints. Once the surgical port is in about the correct pose (e.g., position and orientation), the physician closes one or more latches of the holding arm to lock the joints thereof. This process takes time, involves radiation (to determine whether the surgical port is properly aligned with the target anatomy), and may need to be repeated several times during a procedure (e.g., if multiple incisions must be utilized to reach multiple target anatomies). Moreover, known holding arms are hard to maneuver and the mechanisms for tightening or locking the arm into place can displace the surgical port, resulting in some degree of inaccuracy in placement of the surgical port.

According to embodiments of the present disclosure, a surgeon may plan a surgical procedure on a robotic platform (or using any computer with a user interface, and providing the plan to a robotic platform). The patient anatomy may be registered to the robotic platform (e.g., by registering a coordinate system of the patient to a coordinate system of the robotic platform). An insertion vector may then be calculated, based on, for example, the surgical procedure described in the surgical plan as well as any needed tools for that procedure. A robotic arm of the robot is then caused to hold a surgical port in a pose that corresponds to the insertion vector. Any tools needed to hold the surgical port open may be inserted into or otherwise held in proper position by the robotic arm.

When a force is applied to the surgical port (e.g., by the soft tissue of the patient, by a surgeon manipulating one or more tools within the surgical port, or otherwise), the robotic arm maintains the surgical port in the proper pose. If the force is excessive (e.g., as compared to a predetermined threshold, and as measured by one or more sensors on the robotic arm or elsewhere), then a user alert may be generated.

In such embodiments, the surgical procedure takes place via the surgical port, whether manually, or using the robot. The same robotic arm used to hold the surgical port in a proper pose may also be used to carry out some or all of the surgical procedure, or one or more additional robotic arms may be used to assist with or carry out the surgical procedure via the surgical port. When a force applied on the surgical port by one or more additional robotic arms is detected, or when a force applied on the surgical port by a surgeon manually completing the surgical procedure is detected, the robotic arm holding the surgical port may be controlled or otherwise manipulated to maintain the surgical port in the proper pose, and/or the one or more additional robotic arms may be controlled or otherwise manipulated to reduce the applied force, and/or a user alert may be generated.

If, during the surgical procedure, a planned or an unplanned change of work trajectory is required (such that a new pose of the surgical port is needed), the robot holding the port may change the vector of the surgical port accordingly, either while holding the port itself or by removing the port pieces, moving those pieces, and then reassembling those pieces.

Embodiments of the present disclosure provide technical solutions to the problems of (1) reducing the size of incisions required for MIS procedures; (2) reducing the amount of time required for (and thus the cost of) setup in preparation for a minimally invasive and/or endoscopic surgery; (4) improving the accuracy of instrument positioning in preparation for minimally invasive and/or endoscopic surgery; and/or (5) increasing patient safety during robot-assisted or robotic minimally invasive and/or endoscopic surgeries.

Figure 1:
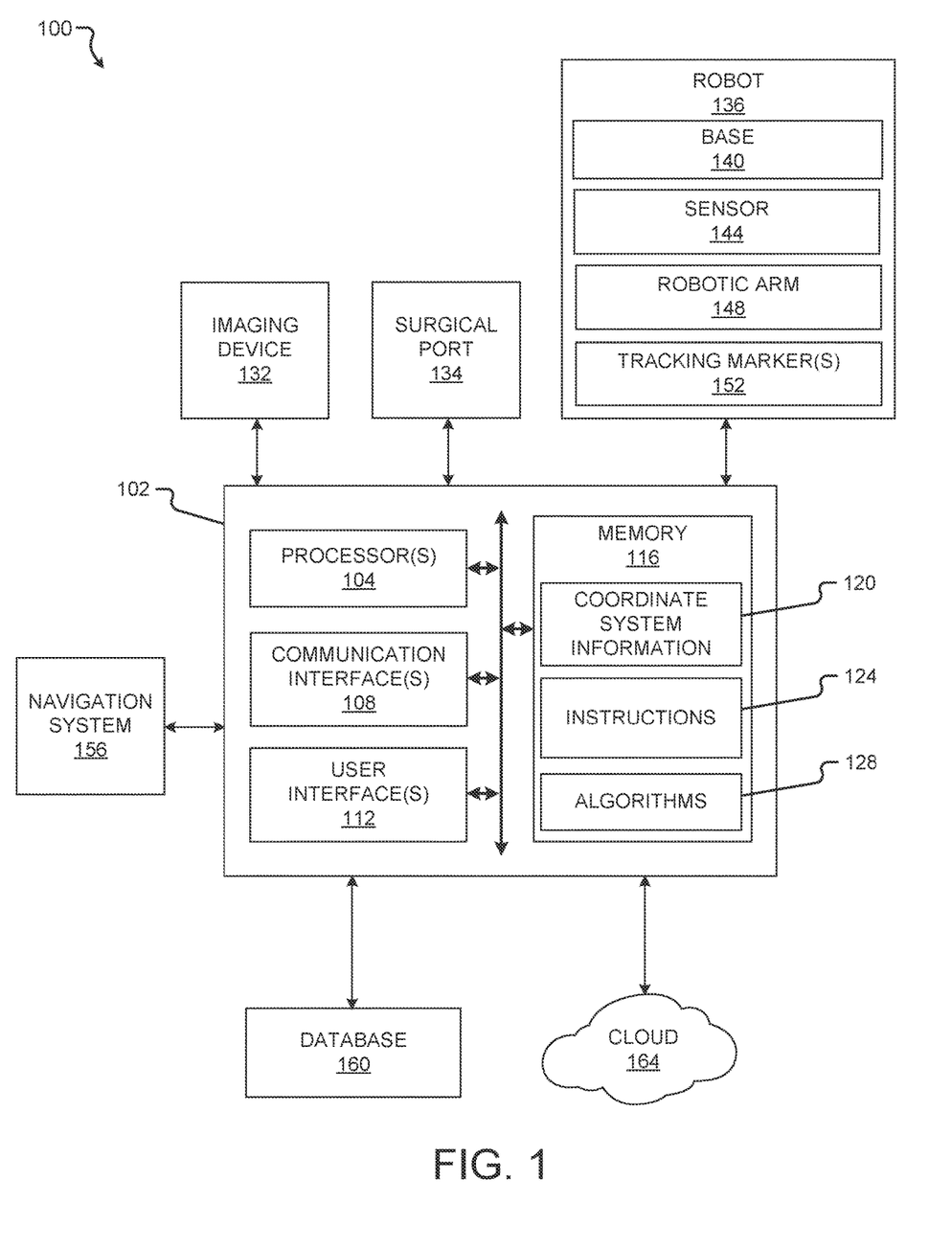
FIG. 1 is a block diagram of a system according to at least one embodiment of the present disclosure.

Turning first to FIG. 1, a block diagram of a system 100 according to at least one embodiment of the present disclosure is shown. The system 100 may be used, for example: to hold an MIS port in a proper pose during an MIS procedure; to determine a proper pose for an MIS port during an MIS procedure; to carry out one or more aspects of one or more of the methods disclosed herein; for navigation purposes; for registration purposes; to carry out a fully autonomous and/or a robot-assisted surgery using a plurality of robots; or for any other useful purpose. The system 100 comprises a computing device 102, an imaging device 132, a surgical port 134, a robot 136, a navigation system 156, a database 160, and a cloud 164. Notwithstanding the foregoing, systems according to other embodiments of the present disclosure may omit any one or more of the computing device 102, the imaging device 132, the robot 136, the navigation system 156, the database 160, and/or the cloud 164. Additionally, systems according to other embodiments of the present disclosure may arrange one or more components of the system 100 differently (e.g., one or more of the imaging device 132, the surgical port 134, the robot 136, and/or the navigation system 156 may comprise one or more of the components shown in FIG. 1 as being part of the computing device 102 or any of the other components of the system 100). Still further, systems according to other embodiments of the present disclosure may comprise two or more of any of the components described herein, including, for example, the imaging device 132, the surgical port 134, the robot 136, and/or the database 160.

The computing device 102 comprises at least one processor 104, at least one communication interface 108, at least one user interface 112, and at least one memory 116. A computing device according to other embodiments of the present disclosure may omit one or both of the communication interface(s) 108 and the user interface(s) 112.

The at least one processor 104 of the computing device 102 may be any processor identified or described herein or any similar processor. The at least one processor 104 may be configured to execute instructions stored in the at least one memory 116, which instructions may cause the at least one processor 104 to carry out one or more computing steps utilizing or based on data received, for example, from the imaging device 132, the robot 136, the navigation system 156, the database 160, and/or the cloud 164.

The computing device 102 may also comprise at least one communication interface 108. The at least one communication interface 108 may be used for receiving image data or other information from an external source (such as an imaging device 132, a robot 136, the navigation system 156, the database 160, the cloud 164, and/or a portable storage medium (e.g., a USB drive, a DVD, a CD)), and/or for transmitting instructions, images, or other information from the at least one processor 104 and/or the computing device 102 more generally to an external system or device (e.g., another computing device 102, the imaging device 132, the robot 136, the navigation system 156, the database 160, the cloud 164, and/or a portable storage medium (e.g., a USB drive, a DVD, a CD)). The at least one communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, Bluetooth low energy, NFC, ZigBee, and so forth). In some embodiments, the at least one communication interface 108 may be useful for enabling the computing device 102 to communicate with one or more other processors 104 or computing devices 102, whether to reduce the time needed to accomplish a computing-intensive task or for any other reason.

The at least one user interface 112 may be or comprise a keyboard, mouse, trackball, monitor, television, touchscreen, button, joystick, switch, lever, and/or any other device for receiving information from a user and/or for providing information to a user of the computing device 102. The at least one user interface 112 may be used, for example, to receive a user selection or other user input in connection with any step of any method described herein; to receive a user selection or other user input regarding one or more configurable settings of the computing device 102, the imaging device 132, the robot 136, and/or of another component of the system 100; to receive a user selection or other user input regarding how and/or where to store and/or transfer data received, modified, and/or generated by the computing device 102; and/or to display information (e.g., text, images) and/or play a sound to a user based on data received, modified, and/or generated by the computing device 102. Notwithstanding the inclusion of the at least one user interface 112 in the system 100, the system 100 may automatically (e.g., without any input via the at least one user interface 112 or otherwise) carry out one or more, or all, of the steps of any method described herein.

Although the at least one user interface 112 is shown as part of the computing device 102, in some embodiments, the computing device 102 may utilize a user interface 112 that is housed separately from one or more remaining components of the computing device 102. In some embodiments, the user interface 112 may be located proximate one or more other components of the computing device 102, while in other embodiments, the user interface 112 may be located remotely from one or more other components of the computer device 102.

The at least one memory 116 may be or comprise RAM, DRAM, SDRAM, other solid-state memory, any memory described herein, or any other tangible non-transitory memory for storing computer-readable data and/or instructions. The at least one memory 116 may store information or data useful for completing, for example, any step of the methods 200 or 300 described herein. The at least one memory 116 may store, for example, information about one or more coordinate systems 120 (e.g., information about a robotic coordinate system or space corresponding the robot 136, information about a navigation coordinate system or space, information about a patient coordinate system or space); instructions 124 for execution by the at least one processor 104, for example to cause the at least one processor 104 to carry out one or more of the steps of the methods 200 and/or 300; and/or one or more algorithms 128 for use by the processor in carrying out any calculations necessary to complete one or more of the steps of the methods 200 and/or 300 (e.g., to calculate an insertion vector, determine a pose, register one coordinate system to another, and so forth), or for any other calculations. Such predetermined coordinate system(s) information 120, instructions 124, and/or algorithms 128 may, in some embodiments, be organized into one or more applications, modules, packages, layers, or engines, and may cause the at least one processor 104 to manipulate data stored in the at least one memory 116 and/or received from or via another component of the system 100.

The imaging device 132 may be operable to image anatomical feature(s) (e.g., a bone, veins, tissue, etc.) and/or other aspects of patient anatomy, and/or any surgical instruments or tools within the field of view of the imaging device 132, to yield image data (e.g., image data depicting or corresponding to a bone, veins, tissue, implants, tools, etc.). The imaging device 132 may be capable of taking a 2D image or a 3D image to yield the image data. "Image data" as used herein refers to the data generated or captured by an imaging device 132, including in a machine-readable form, a graphical/visual form, and in any other form. In various examples, the image data may comprise data corresponding to an anatomical feature of a patient, or to a portion thereof. The imaging device 132 may be or comprise, for example, an ultrasound scanner (which may comprise, for example, a physically separate transducer and receiver, or a single ultrasound transceiver), a radar system (which may comprise, for example, a transmitter, a receiver, a processor, and one or more antennae), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography scanner, an endoscope, a telescope, a thermographic camera (e.g., an infrared camera), or any other imaging device 132 suitable for obtaining images of an anatomical feature of a patient.

In some embodiments, the imaging device 132 may comprise more than one imaging device 132. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 132 may be operable to generate a stream of image data. For example, the imaging device 132 may be configured to operate with an open shutter, or with a shutter that continuously alternates between open and shut so as to capture successive images.

The surgical port 134 may be or comprise any surgical port through which one or more surgical tools may be inserted to access a surgical site. The surgical port 134 may be, for example, an MIS port or an endoscopic port. The surgical port 134 may be a single-piece port having fixed dimensions, a multi-piece port requiring assembly but having fixed dimensions, or a multi-piece port with adjustable dimensions. The surgical port 134 may, in some embodiments, comprise one or more sensors such as the sensors 144 described below. The surgical port 134 may be configured to be secured to, held by, or otherwise manipulated by the robot 136, and more particularly by the robotic arm 148.

The robot 136 may be any surgical robot or surgical robotic system. The robot 136 may be or comprise, for example, the Mazor X™ Stealth Edition robotic guidance system. The robot 136 may comprise a base 140 that supports a robotic arm 148. The robot 136 may comprise one or more robotic arms 148 (e.g., some robots 136 may comprise two robotic arms 148, three robotic arms 148, four robotic arms 148, or another number of robotic arms 148). Each robotic arm 148 may, in some embodiments, assist with a surgical procedure (e.g., by holding a surgical port 134 or surgical tool in a desired trajectory or pose and/or supporting the weight of a tool while another robotic arm 148, robot 136, a surgeon, or another medical professional operates the tool) and/or automatically carry out a surgical procedure.

Each robotic arm 148 may have three, four, five, six, or more degrees of freedom.

The robot 136 also comprises one or more sensors 144. The sensor 144 may be a force sensor, configured to detect a force applied on the robotic arm 148 (e.g., whether via an end effector of the robotic arm 148, a tool held by an end effector of the robotic arm 148, or otherwise). The sensor 144 may be a position sensor, a proximity sensor, a magnetometer, or an accelerometer. In some embodiments, the sensor 144 may be a linear encoder, a rotary encoder, or an incremental encoder. In still other embodiments, the sensor 144 may be an imaging sensor. Other types of sensors may also be used as the sensor 144. The one or more sensors 144 may be positioned, for example, on the robotic arm 148 or elsewhere.

Data from the sensor(s) 144 may be provided to a processor of the robot 136, to the processor 104 of the computing device 102, and/or to the navigation system 156. The data may be used to calculate a position in space of the robotic arm 148 relative to one or more coordinate systems (e.g., based on coordinate system information 120 stored in the memory 116). The calculation may be based not just on data received from the sensor(s) 144, but also on data or information (such as, for example, physical dimensions) about, for example, the robot 136 or a portion thereof, or any other relevant object, which data or information may be stored, for example, in a memory 116 of a computing device 102 or in any other memory.

One or more tracking markers 152 may be fixedly secured to or positioned on the robot 136, whether on the base 140, the robotic arm 148, and/or elsewhere. In some embodiments, one or more tracking markers 152 may additionally or alternatively be affixed to one or more other components of the system 100. The tracking markers 152 may be useful for enabling the navigation system 156 to determine and/or track a position of the robot 136 (or any other component to which one or more tracking markers 152 are secured).

The navigation system 156 of the system 100 may provide navigation for a surgeon and/or for the robot 136 during an operation. The navigation system 156 may be any now-known or future-developed navigation system, including, for example, the Medtronic StealthStation™ S8 surgical navigation system. The navigation system 156 may include a camera or other sensor(s) for detecting and/or tracking one or more reference markers, navigated tracking markers, or other objects within an operating room or other room where a surgical procedure takes place. In various embodiments, the navigation system 156 may be used to track a position of the surgical port 134 or the robotic arm 148 (or, more particularly, of one or more tracking markers 152 attached to the surgical port 134 or robotic arm 148). The navigation system 156 may be used to track a position of one or more reference frames, markers, or arrays or other structures useful for detection by a camera or other sensor of the navigation system 156. The navigation system 156 may be used, for example, to detect a position of a reference frame mounted to a patient and/or a position of one or more robotic arms 148, and to register or otherwise correlate a patient coordinate system to a robotic coordinate system based at least on the detected positions. The navigation system 156 may include a display for displaying one or more images from an external source (e.g., the computing device 102, the imaging device 132, a database 160, the cloud 164, or another source) or a video stream from the camera or other sensor of the navigation system 156. In some embodiments, the system 100 may operate without the use of the navigation system 156.

The database 160 may store information that correlates one coordinate system to another (e.g., one or more robotic coordinate systems to a patient coordinate system and/or to a navigation coordinate system). The database 160 may additionally or alternatively store, for example, information about or corresponding to one or more characteristics of the tracking markers 152; one or more surgical plans (including, for example, image information about a patient's anatomy at and/or proximate the surgical site, for use by the robot 136, the navigation system 156, and/or a user of the computing device 102 or of the system 100); one or more images useful in connection with a surgery to be completed by or with the assistance of one or more other components of the system 100; and/or any other useful information. The database 160 may be configured to provide any such information to the computing device 102 or to any other device of the system 100 or external to the system 100, whether directly or via the cloud 164. In some embodiments, the database 160 may be or comprise part of a hospital image storage system, such as a picture archiving and communication system (PACS), a health information system (HIS), and/or another system for collecting, storing, managing, and/or transmitting electronic medical records including image data.

The cloud 164 may be or represent the Internet or any other wide area network. The computing device 102 may be connected to the cloud 164 via the communication interface 108, using a wired connection, a wireless connection, or both. In some embodiments, the computing device 102 may communicate with the database 160 and/or an external device (e.g., a computing device) via the cloud 164.

Figure 2:
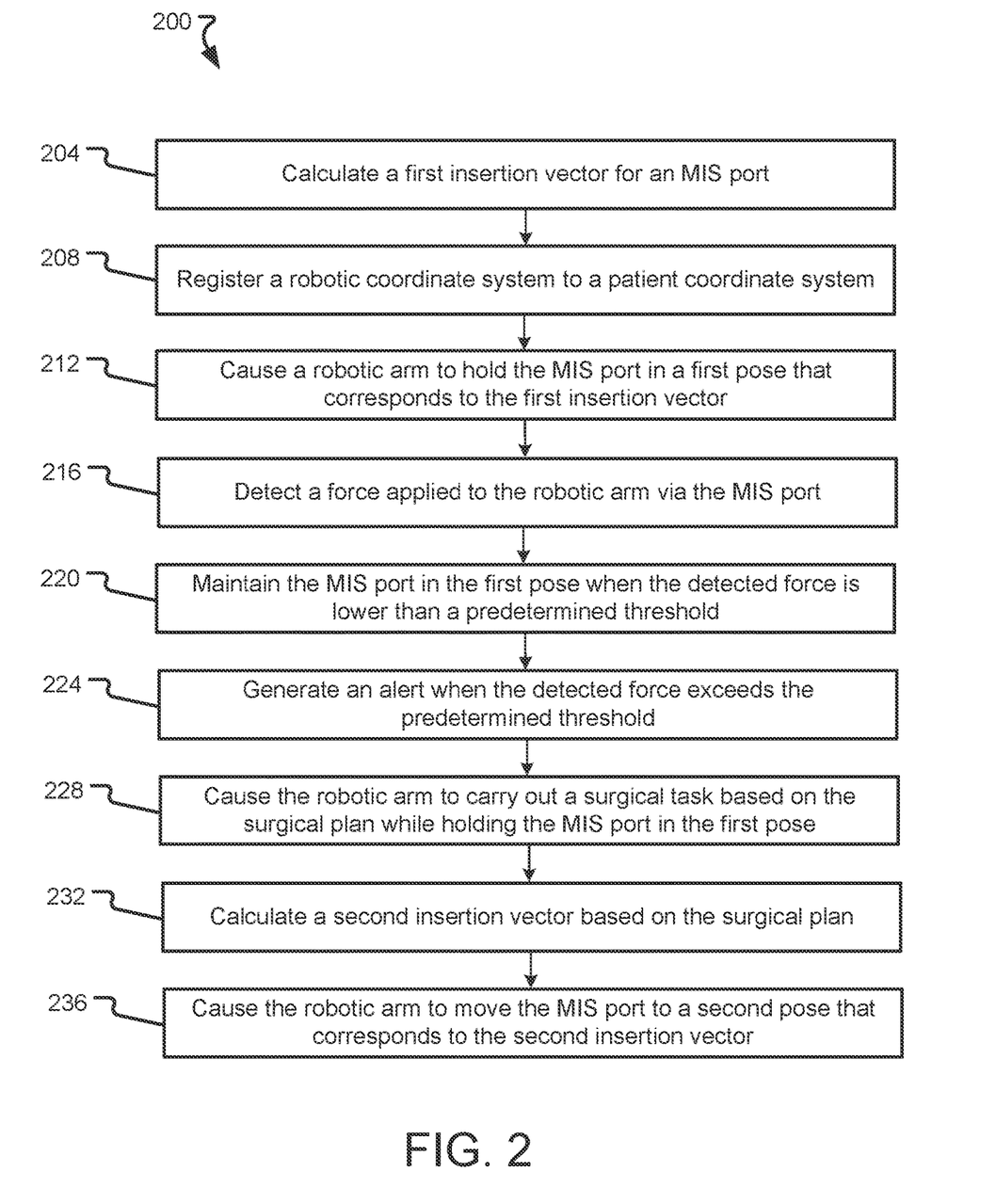
FIG. 2 is a flowchart of a method according to at least one embodiment of the present disclosure.

FIG. 2 depicts a method 200 for a robot-assisted minimally invasive surgery. The method 200 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 136) or part of a navigation system (such as a navigation system 156). A processor other than any processor described herein may also be used to execute the method 200. The at least one processor may perform the method 200 by executing instructions stored in a memory, such as the instructions 124 of the memory 116. The instructions may correspond to one or more steps of the method 200 described below. The instructions may cause the processor to execute one or more algorithms, such as the algorithms 128. For example, one or more such algorithms 128 may be used to determine an insertion vector and/or a correct pose of an MIS port (or any other surgical port 134) based on a surgical plan, to register one coordinate system to another coordinate system, to compare a detected or other force to a predetermined threshold, and/or to control a robotic arm based on a detected or other force.

The method 200 comprises calculating a first insertion vector for an MIS port (step 204). The MIS port may be the same as or similar to the surgical port 134. The calculating may be based on a surgical plan, which may be stored in a memory such as the memory 116 and/or a database such as the database 160, and/or may be received via a network such as the cloud 164 and/or via a communication interface such as the communication interface 108. The surgical plan may describe, for example, a minimally invasive surgery or portion thereof, and may identify one or more of a skin incision location, a target anatomy, a tool to be used during the minimally invasive surgery, and/or a sequence of surgical tasks to be carried out during the minimally invasive surgery. The calculating the first insertion vector for the MIS port may comprise determining, based on the surgical plan, a trajectory or insertion vector from the skin incision to the target anatomy, along which one or more tools will need to extend to reach the target anatomy. The first insertion vector may be calculated in two dimensions in some embodiments, and in three dimensions in other embodiments.

According to some embodiments of the present disclosure, the first insertion vector may be calculated based on information from the surgical plan about the target anatomy and/or one or more additional pieces of information, whether about one or more surgical tools to be used in the procedure, one or more surgeon preferences, historical data regarding similar procedures, or otherwise. The first insertion vector may be calculated before any skin incision location is calculated or otherwise determined. In some embodiments, the method 200 further comprises determining a skin incision location based on the first insertion vector, and/or determining a recommended incision length based on the first insertion vector and/or other information in the surgical plan.

In some embodiments, the calculating may also be based on real-time (or otherwise current) information about a relative position of a skin incision and the target anatomy. Because the position of the skin (relative, e.g., to a patient's internal anatomy) may change based on a pose of a patient, one or more of an imaging device such as the imaging device 132 and/or one or more tracking markers such as the tracking markers 152 may be used to determine a relative position of the skin incision to the internal target anatomy. This information may then be used to calculate an insertion vector that is appropriate in light of the patient's current pose. Additionally or alternatively, the first insertion vector may be calculated to pass within a predetermined distance from a known position of a skin incision, with the understanding that due to the flexibility of skin, the skin incision may be moved (whether manually be a surgeon, automatically by a robot moving an MIS port inserted into the skin incision, or otherwise) from its current location.

The calculated insertion vector is a vector along which an MIS port may be inserted into a skin incision such that the MIS port is properly positioned to guide one or more tools inserted therein along a proper trajectory to reach a target anatomical element or volume. In some embodiments, multiple target anatomical elements or volumes may be reachable from a single incision. In such embodiments, a separate insertion vector may be calculated for each target anatomical element or volume, as described in greater detail below.

The method 200 also comprises registering a robotic coordinate system to a patient coordinate system (step 208). Such registration correlates a robotic coordinate system (e.g., a coordinate system in which one or more robotic arms of a robot are controlled) to a patient coordinate system (e.g., a coordinate system that can be used to define a precise position and/or orientation of every anatomical feature of a patient). In some embodiments, the registration may utilize one or more images, including, for example, a virtual model of patient anatomy, an image of a patient or a portion thereof in a current pose, and/or an image of a robotic arm holding a reference frame, or a combination of two or more of the foregoing. In some embodiments, data generated by one or more sensors other than an optical sensor may be used instead of images. In other embodiments, the method 300 may comprise registering a robot coordinate system and a patient coordinate system to a navigation coordinate system used by a navigation system such as the navigation system 156.

Where a skin incision (e.g., into which an MIS port will be inserted for the surgical procedure described in the surgical plan of the step 204) has not already been made, the method 200 may comprise utilizing a robotic arm (e.g., a robotic arm 148) to identify a recommended skin incision location and length. In some embodiments, the robotic arm may comprise or hold a laser pointer, which may be manipulated by the robotic arm to identify the endpoints and/or the entire length of a recommended incision. In other embodiments, the robotic arm may comprise or hold a marker or other device for marking a patient's skin with a recommended location for a skin incision. In still other embodiments, the robotic arm may comprise or hold a scalpel or other cutting tool, and may make a skin incision at the recommended location and of the recommended length. Additionally, although the foregoing description refers to a recommended location and length for a skin incision (e.g., generated by a processor), in some embodiments the location and/or length of a needed skin incision may be determined by a surgeon or other user, and provided to the processor via a user interface such as the user interface 112.

The method 200 also comprises causing a robotic arm to hold the MIS port in a first pose that corresponds to the first insertion vector (step 212). The robotic arm may be the same as or similar to the robotic arm 148 described above. The MIS port may be any MIS port able to be held by the robotic arm and/or selected by the surgeon or other user. The MIS port may be a single-piece MIS port, or may comprise a plurality of pieces that are assembled either prior to or after insertion of the MIS port into a skin incision. In embodiments where the MIS port comprises a plurality of pieces, the robotic arm may be configured to autonomously assemble the MIS port, or the MIS port may be assembled manually (whether before or after attachment thereof to the robotic arm). The first pose may be a pose that aligns an axis of the MIS port with the first insertion vector (e.g., such that the axis of the MIS port extends along the first insertion vector).

The step 212 may comprise calculating or otherwise determining the first pose. The first pose may be determined based on the insertion vector as well as one or more dimensions of the MIS port, the robotic arm, and/or any end effector or other connector used to secure the MIS port to the robotic arm. The first pose may be calculated to ensure that the MIS port is inserted into a skin incision of the patient to the proper depth. The calculating may utilize one or more algorithms such as the algorithms 128.

In some embodiments, the MIS port may be attached to the robotic arm before the robotic arm is moved into a pose that will result in the robotic arm holding the MIS port in the first pose (e.g., after the MIS port is secured to the robotic arm, the robotic arm may be maneuvered to cause the robotic arm to hold the MIS port in the first pose). In other embodiments, the robotic arm may be moved to a particular pose, which particular pose may be selected so that when the MIS port is attached to the robotic arm, the MIS port is in the first pose (e.g., the robotic arm is first moved to wherever it needs to be to hold the MIS port in the first pose, and then the MIS port is attached to the robotic arm).

The step 212 may also comprise generating one or more instructions or other signals that cause one or more motors or other actuators of the robotic arm to maneuver the robotic arm into a position that enables the robotic arm to hold the MIS port in the first pose. The step 212 may further comprise continuing to generate one or more instructions or other signals that cause the one or more motors or other actuators of the robotic arm to operate in response to one or more forces applied on the MIS port and/or the robotic arm, so as to hold the MIS port in the first pose despite the application of one or more forces to the MIS port and/or the robotic arm.

The method 200 also comprises detecting a force applied to the robotic arm via the MIS port (step 216). The force may be applied by the soft tissue of the patient, whether due to a pose of the patient or otherwise. The force may additionally or alternatively be applied by one or more tools extending through the MIS port and pushing against the MIS port, in any direction. The force may be applied by the patient on the MIS port as a result of the patient's breathing motion. The force may also result from accidental contact between a surgeon or other user and the MIS port or the arm itself. Although the step 216 is described as detecting a force applied to the robotic via the MIS port, in some embodiments the force may be applied directly to the robotic arm, or the force may be applied to the robotic arm via a component other than the MIS port.

The force may be detected with a sensor such as a sensor 144. The detected force may be or comprise a linear force, rotational force (e.g., torque), and/or any other type of force.

The sensor may be positioned on the robotic arm or elsewhere. The sensor may be configured to detect motion of the robotic arm and to calculate a force based on information about a stiffness of the robotic arm as well as the detected motion. Alternatively, the sensor may be configured to measure force directly. Any type of sensor capable of direct measurement of force, or of calculation of force based on some other measurement, may be used to detect the force for purposes of the step 216. In some embodiments, the detected force may comprise one or more individual force components (e.g., a force component in each of an X-axis, a Y-axis, and a Z-axis, and/or a torque component around an X-axis, a Y-axis, and a Z-axis).

Although the step 216 is described as detecting a force applied to the robotic arm via the MIS port, in some embodiments, the step 216 may be or comprise detecting an unintended movement of the MIS port from the first pose. In such embodiments, the robotic arm may move the MIS port back to the first pose (e.g., if the MIS port is within a given distance from the first pose, and/or if there is not currently a tool extending through the MIS port), or may generate an alert (as described, for example, in connection with the step 224).

The method 200 also comprises maintaining the MIS port in the first pose when the detected force is lower than a predetermined threshold (step 220). The predetermined threshold may be based on one or more characteristics of the MIS port, the robotic arm, and/or a connection between the MIS port and the robotic arm. In some embodiments, the predetermined threshold may be calculated to be lower than a magnitude of force that would result in damage to the MIS port, the robotic arm, and/or the connection therebetween. In other embodiments, the predetermined threshold may be calculated to be equal to or lower than a maximum responsive force that the robotic arm can exert on the MIS port, so as to prevent movement of the MIS port as a result of the forces applied thereon. In still other embodiments, the predetermined threshold may be calculated based on one or more patient characteristics. For example, the predetermined threshold may be higher than the force exerted on the MIS port or the robot as a result of the patient's normal breathing (which force may be expected to repeatedly occur throughout the surgical procedure). In yet further embodiments, the predetermined threshold corresponds to a maximum force expected during a surgical procedure involving the MIS port. The predetermined threshold may alternatively be determined based on any combination of the foregoing factors and/or any other factors.

The step 220 may comprise comparing the detected force to the predetermined threshold. The comparing may comprise comparing a single combined force vector to a predetermined threshold, and/or comparing individual force components to individual force thresholds. The detected force may be considered to be lower than the predetermined threshold if the overall force vector has a lower magnitude than the predetermined threshold, or the detected force may be considered to be lower than the predetermined threshold if any individual force component exceeds a corresponding predetermined threshold component (and/or regardless of whether the overall force vector has a lower magnitude than the predetermined threshold).

Additionally, in some embodiments, the predetermined threshold may comprise a threshold magnitude that depends on a direction of the detected force vector. Thus, for example, the predetermined threshold may comprise a first threshold magnitude for a force exerted in a first direction, and a second threshold magnitude different than the first threshold magnitude for a force exerted in a second direction different than the first direction. The different threshold magnitudes may be based, for example, on an ability of the robotic arm to generate a counteractive force in each direction (which may be different for different directions). Also, as referenced above, the predetermined threshold may comprise individual components (e.g., in the X-axis, Y-axis, and Z-axis directions, and/or around the X-axis, the Y-axis, and the Z-axis) or may simply comprise an overall threshold magnitude and direction. In still other embodiments, the predetermined threshold may comprise only a threshold magnitude.

The step 220 may further comprise generating one or more instructions or other signals that cause the one or more motors or other actuators of the robotic arm to operate in response to the one or more detected forces, so as to generate a resistive force that counteracts the detected force and thus holds the MIS port in the first pose despite the detected force. In some embodiments, the robotic arm may have a response time (between detection of a force and generation of a resistive force that counteracts the detected force) of less than 500 ms, or less than 250 ms, or less than 100 ms, or less than 50 ms, or less than 10 ms.

Also in some embodiments, the step 220 may comprise maintaining the MIS port in the first pose relative to the patient. Thus, for example, where a patient's breathing causes constant and predictable motion of a relevant portion of the patient's anatomy, the step 220 may comprise generating one or more instructions or other signals that cause the one or more motors or other actuators of the robotic arm to move the MIS port up and down (or in any other manner) in sequence with the patient's breathing so as to maintain the MIS port in the first pose relative to the patient. In such embodiments, the patient's breathing may be detected during the step 216 (e.g., by tracking the forces exerted on the MIS port for a period of time once the MIS port is in the first pose), and using the data gathered to determine needed movement of the MIS port to reduce or eliminate the detected forces. Alternatively, an average or halfway position (e.g., a position where the repeated cyclical forces resulting from the patient's breathing sum to zero or near zero) may be determined, and the MIS port may be maintained in the first pose at that position.

In still further embodiments, one or more external sensors (whether imaging sensors, force sensors, or otherwise) may be used to detect movement of a patient due to the patient's breathing, which detected movement may then be used for purposes of the step 220 as described above.

The step 220 occurs automatically (e.g., without manual involvement). The step 220 may beneficially result in the MIS port remaining substantially stationary (e.g., within clinical tolerances for a given surgery) during use thereof for a minimally invasive surgical procedure. The ability of the robotic arm to respond to applied forces that would otherwise cause movement of the MIS port, together with the ability of the robotic arm to move the MIS port back to the same position essentially immediately after the MIS port has been displaced, represents a significant improvement over existing options for holding an MIS port, and results in significant time (and thus cost) savings.

The method 200 also comprises generating an alert when the detected force exceeds the predetermined threshold (step 224). The alert may be an audible alert (e.g., a warning horn, a siren, a beep, a spoken warning, and/or any other audible alert), a visual alert (e.g., a flashing light, text displayed on a screen), a change in color of a displayed graphic, and/or any other visual alert), a tactile alert (e.g., a buzzing of one or more surgical instruments), or any other alert or combination thereof. In some embodiments, the alert may be accompanied by the retraction of the MIS port from the patient, and/or by causing the robotic arm holding the MIS port and/or any other robotic arm being used to assist with the MIS procedure to stop all movement. The alert may be provided, in whole or in part, via a user interface such as the user interface 112.

Where, for example, the predetermined threshold is based at least in part on the force(s) exerted on the MIS port and/or robotic arm as a result of the patient's normal breathing, then abnormal breathing or other unexpected patient movement may result in exertion of a force that exceeds the predetermined threshold and results in generation of an alert.

In some embodiments, the step 224 may comprise generating an alert when the MIS port has experienced an uncommanded movement (e.g., due to application of an external force on the MIS port and/or the robotic arm holding the MIS port) out of the first pose. In such embodiments, the alert may be any alert described above, and may be generated regardless of the magnitude (e.g., distance and/or angle of rotation) of the movement, or only if the movement exceeds a threshold magnitude.

The method 200 also comprises causing the robotic arm to carry out a surgical task based on the surgical plan while holding the MIS port in the first pose (step 228). The surgical task may be any step of a minimally invasive surgical procedure, and may involve the use of one or more minimally invasive tools. More specifically, the surgical task may comprise manipulating a tool that extends through the MIS port being held by the robotic arm. The surgical task may comprise holding a tool in the MIS port and/or extending a tool into the MIS port. The tool may be, for example, a drill, tap, screwdriver, saw, or any other tool. The robotic arm may, in some embodiments, be used to carry out an entire surgical procedure via the MIS port. In other embodiments, the robotic arm may be used to carry out one or more tasks of an MIS surgical procedure, while a surgeon or other medical personnel may carry out one or more other tasks of the MIS surgical procedure.

To carry out the step 228, the MIS port may be supported at a first location of the robotic arm, and a tool or other medical device may be held or otherwise secured to the robotic arm at a second location on the robotic arm. The second location may be movable relative to the first location, such that the MIS port can be held in the first pose while the robotic arm manipulates the tool or other medical device within the MIS port.

The method 200 also comprises calculating a second insertion vector based on the surgical plan (step 232). Where the surgical plan describes an MIS procedure that cannot be completed through an MIS port in a single pose, the MIS port may need to be moved one or more times in order to access additional anatomical targets. For such MIS procedures, one or more additional insertion vectors may be calculated based on the surgical plan. The number of insertion vectors may depend, therefore, on how many insertion vectors are needed to achieve access to each anatomical target identified in the surgical plan. The second insertion vector of the step 232 is different than the first insertion vector of the step 204.

In some embodiments, more than one insertion vector may pass through a single skin incision. In such embodiments, the MIS port may simply be moved within a skin incision. In other embodiments, one or more insertion vectors may not pass through the same skin incision, such that more than one skin incision is required to position the MIS port along each insertion vector at the appropriate time during the MIS procedure. In such embodiments, the MIS port may be moved from one incision to another.

The method 200 also comprises causing the robotic arm to move the MIS port to a second pose that corresponds to the second insertion vector (step 236). As described above, the MIS port may be a single-piece MIS port, or may comprise a plurality of pieces that are assembled either prior to or after insertion of the MIS port into a skin incision. In embodiments where the MIS port comprises a plurality of pieces, the robotic arm may be configured to autonomously disassemble the MIS port in the first pose, move the MIS port pieces, and reassemble the MIS port in the second pose. Alternatively, the MIS port may be disassembled and then reassembled manually. The second pose may be a pose that aligns an axis of the MIS port with the second insertion vector (e.g., such that the axis of the MIS port extends along the second insertion vector).

The step 236 may comprise calculating or otherwise determining the second pose. The second pose may be determined in the same manner as the first pose, as described above. Although the step 236 is described as causing the robotic arm to move the MIS port to the second pose, in some embodiments, the MIS port is detached from the robotic arm, the robotic arm is moved to a pose that corresponds to the second pose, and the MIS port is reattached to the robotic arm in the second pose.

The step 236 may also comprise generating one or more instructions or other signals that cause one or more motors or other actuators of the robotic arm to maneuver the robotic arm into a position that enables the robotic arm to hold the MIS port in the second pose. The step 236 may further comprise continuing to generate one or more instructions or other signals that cause the one or more motors or other actuators of the robotic arm to operate in response to one or more forces applied on the MIS port and/or the robotic arm, so as to hold the MIS port in the second pose despite the application of one or more forces to the MIS port and/or the robotic arm.

The present disclosure encompasses embodiments of the method 200 that comprise more or fewer steps than those described above, and/or one or more steps that are different than the steps described above.

Figure 3:
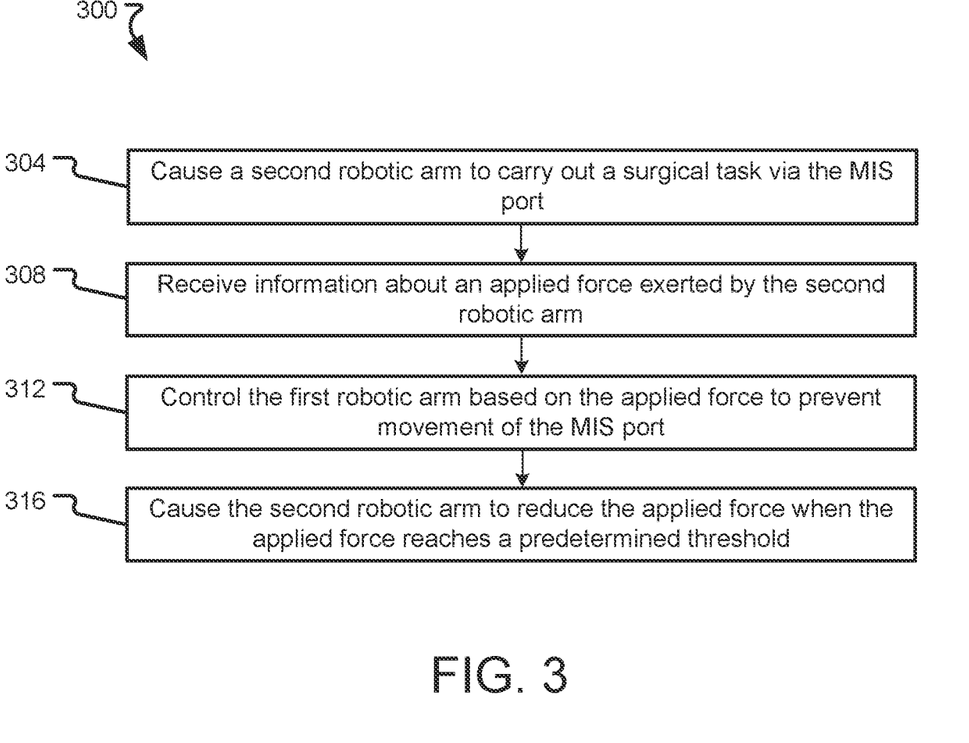
FIG. 3 is another flowchart of a method according to at least one embodiment of the present disclosure.

Turning now to FIG. 3, a method 300 of utilizing a second robotic arm in connection with a robotically held MIS port may be carried out or otherwise performed, for example, by at least one processor. The at least one processor may be the same as or similar to the processor(s) 104 of the computing device 102 described above. The at least one processor may be part of a robot (such as a robot 136) or part of a navigation system (such as a navigation system 156). A processor other than any processor described herein may also be used to execute the method 300. The at least one processor may perform the method 300 by executing instructions stored in a memory, such as the instructions 124 of the memory 116. The instructions may correspond to one or more steps of the method 300 described below. The instructions may cause the processor to execute one or more algorithms, such as the algorithms 128. For example, one or more such algorithms 128 may be used to map one coordinate system to another coordinate system once each coordinate system has been located.

The method 300 comprises causing a second robotic arm to carry out a surgical task via the MIS port (step 304). The MIS port may be the same MIS port described above in connection with the method 200, or any other surgical port 134. Moreover, the MIS port as referenced in connection with the method 300 is being held by a first robotic arm, such as the robotic arm described in connection with the method 200. The second robotic arm is another robotic arm, different than the robotic arm holding the MIS port, that is configured to manipulate one or more tools or other medical devices so as to carry out a surgical task via the MIS port while the MIS port is being held by the first robotic arm.

The surgical task may be any step of a minimally invasive surgical procedure, and may involve the use of one or more minimally invasive tools. More specifically, the surgical task may comprise manipulating a tool that extends through the MIS port being held by the first robotic arm. The surgical task may comprise holding a tool in the MIS port and/or extending a tool into the MIS port. The tool may be, for example, a drill, tap, screwdriver, saw, or any other tool. The second robotic arm may, in some embodiments, be used to carry out an entire surgical procedure via the MIS port. In other embodiments, the second robotic arm may be used to carry out one or more tasks of an MIS surgical procedure, while a surgeon or other medical personnel may carry out one or more other tasks of the MIS surgical procedure.

The method 300 also comprises receiving information about an applied force exerted by the second robotic arm (step 308). The applied force is a force exerted by the second robotic arm or any part thereof on the MIS port. The information may be received, for example, from one or more sensors (e.g., sensors 144) on the second robotic arm. In some embodiments, the information may be calculated from received information corresponding to the second robotic arm. For example, the information about the applied force may be calculated from received information about power draw and/or one or more other operating parameters of motors or other actuators of the second robotic arm, received information about a position and/or a movement of the second robotic arm, and/or any other received information corresponding to the second robotic arm. For purposes of the step 308, the second robotic arm includes any tool attached to the second robotic arm.

In some embodiments, the information about the applied force may be or comprise information about a force expected to be applied in the near future (e.g., within the next second, or 500 ms, or 250 ms, or 100 ms, or 50 ms).

The method 300 also comprises controlling the first robotic arm based on the applied force to prevent movement of the MIS port (step 312). The first robotic arm may be controlled to exert an equal and opposite force to the applied force, so that the net force on the MIS port is zero. Alternatively, the first robotic arm may be controlled to exert a force that, while based on the applied force, is not equal and/or opposite to the applied force, for the purpose of reducing the net force on the MIS port to lower than a predetermined threshold (e.g., the predetermined threshold of the step 220 of the method 200).

Although the step 312 is described as controlling the first robotic arm to prevent movement of the MIS port, in some embodiments of the present disclosure, the step 312 may comprise controlling the first robotic arm to move the MIS port based on the applied force. More specifically, if the applied force results, for example, from the second robotic arm pushing against the MIS port in order to move a tool into a position that conflicts only slightly with a position of the MIS port, then the first robotic arm may be caused to move the MIS port slightly so that the MIS port is out of the way of the second robotic arm (and/or a tool held by the second robotic arm). Due to the flexibility of skin and soft tissue, such movement may not require any modification of the incision into which the MIS port is inserted, and may cause limited, if any, additional trauma to the patient. In such embodiments, the first robotic arm may adjust an orientation of the MIS port so that a central axis thereof still points to the same anatomical target as prior to the movement.

In still further embodiments, the first robotic arm may be controlled jointly with the second robotic arm to make slight adjustments of a pose of the MIS port simultaneously with movements of the second robotic arm. In these embodiments, the second robotic arm and the first robotic arm may move in concert (within a limited area so as to minimize or avoid altogether additional trauma to the patient) to facilitate, for example, access to both sides of a vertebra or to other anatomical targets that are accessible from the same incision. Notably, in contrast to the use of a lockable frame to hold an MIS port in a manually configured orientation, a robotic arm holding an MIS port can easily move the MIS port to multiple poses any number of times without requiring much if any surgeon involvement, thus enabling significant savings of precious operating room and surgeon time, reducing the length of the surgery and the associated trauma and expense to the patient, and otherwise facilitating more efficient surgical procedures.

The method 300 also comprises causing the second robotic arm to reduce the applied force when the applied force reaches a predetermined threshold (step 316). The predetermined threshold may be the same as the predetermined threshold of the step 220 of the method 200, or the predetermined threshold may be a different predetermined threshold. The predetermined threshold may be based on a strength, stiffness, or other characteristic of the MIS port. The predetermined threshold may additionally or alternatively be based on a characteristic of the first robotic arm.

The predetermined threshold may comprise a threshold magnitude that depends on a direction of the detected force vector. Thus, for example, the predetermined threshold may comprise a first threshold magnitude for a force exerted in a first direction, and a second threshold magnitude different than the first threshold magnitude for a force exerted in a second direction different than the first direction. The different threshold magnitudes may be based, for example, on an ability of the first robotic arm to generate a counteractive force in each direction (which may be different for different directions). Also, as referenced above, the predetermined threshold may comprise individual components (e.g., in the X-axis, Y-axis, and Z-axis directions, and/or around the X-axis, the Y-axis, and the Z-axis) or may simply comprise an overall threshold magnitude and direction. In still other embodiments, the predetermined threshold may comprise only a threshold magnitude.

The step 316 may beneficially prevent the second robotic arm from applying a force on the MIS port that is so great as to cause damage to the MIS port, and/or to cause the MIS port to move from its current pose, and/or to cause damage to a patient in which the MIS port is inserted.

The present disclosure encompasses embodiments of the method 300 that comprise more or fewer steps than those described above, and/or one or more steps that are different than the steps described above.

As may be appreciated based on the foregoing disclosure, the present disclosure encompasses methods with fewer than all of the steps identified in FIGS. 2 and 3 (and the corresponding description of the methods 200 and 300), as well as methods that include additional steps beyond those identified in FIGS. 2 and 3 (and the corresponding description of the methods 200 and 300). The present disclosure also encompasses methods that comprise one or more steps from one method described herein, and one or more steps from another method described herein.

Although embodiments of the present disclosure have been described herein with respect to minimally invasive surgery, aspects of the present disclosure are also applicable for endoscopic surgery. Thus, for example, the present disclosure encompasses a method comprising: calculating a first insertion vector for an endoscopy port; registering a robotic coordinate system to a patient coordinate system; causing a robotic arm to hold the endoscopy port in a first pose that corresponds to the first insertion vector; detecting a force applied to the robotic arm via the endoscopy port; maintaining the endoscopy port in the first pose when the detected force is lower than a predetermined threshold; generating an alert when the detected force exceeds the predetermined threshold; causing the robotic arm to carry out a surgical task based on the surgical plan while holding the endoscopy port in the first pose; calculating a second insertion vector based on the surgical plan; and causing the robotic arm to move the endoscopy port to a second pose that corresponds to the second insertion vector. This method may be the same as or similar to the method 200, except that it uses an endoscopy port instead of an MIS port.

Similarly, the present disclosures encompasses a method comprising: causing a second robotic arm to carry out a surgical task via an endoscopy port; receiving information about an applied force exerted by the second robotic arm; controlling the first robotic arm based on the applied force to prevent movement of the endoscopy port; and causing the second robotic arm to reduce the applied force when the applied force reaches a predetermined threshold. This method may be the same as or similar to the method 300, except that it uses an endoscopy port instead of an MIS port.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for robot-assisted minimally invasive surgery, the method comprising:

calculating, based on a surgical plan, an insertion vector for a minimally invasive surgery (MIS) port;

causing a robotic arm holding the MIS port to manipulate the MIS port into a pose that corresponds to the insertion vector;

detecting, with a sensor on the robotic arm, a force applied to the robotic arm via the MIS port;

maintaining the MIS port in the pose when the detected force is lower than a predetermined threshold; and generating an alert when the detected force exceeds the predetermined threshold.

2. The method of claim 1, wherein maintaining the MIS port in the pose comprises causing the robotic arm to apply a responsive force to the MIS port, the responsive force based on the detected force.

3. The method of claim 1, wherein the robotic arm is a first robotic arm and the sensor is a first sensor, the method further comprising:

causing a second robotic arm to carry out a surgical task via the MIS port based on the surgical plan.

4. The method of claim 3, further comprising:

receiving, from a second sensor on the second robotic arm, information about an applied force exerted by the second robotic arm.

5. The method of claim 4, further comprising:

controlling the robotic arm based on the applied force to prevent movement of the MIS port.

6. The method of claim 4, further comprising:

causing the second robotic arm to reduce the applied force when the applied force reaches the predetermined threshold.

7. The method of claim 1, wherein the insertion vector is a first insertion vector and the pose is a first pose, the method further comprising:

calculating a second insertion vector based on the surgical plan; and causing the robotic arm to move the MIS port to a second pose that corresponds to the second insertion vector, the second pose different than the first pose.

8. The method of claim 1, wherein the pose is a first pose, the method further comprising:

causing the robotic arm to move the MIS port to a second pose different than the first pose based on user input.

9. The method of claim 8, wherein the MIS port remains at least partially inside a patient during movement of the MIS port from the first pose to the second pose.

10. The method of claim 1, further comprising:

causing the robotic arm to carry out a surgical task based on the surgical plan while the MIS port in the pose.

11. The method of claim 1, wherein the predetermined threshold is based on forces exerted on the MIS port as a result of breathing motion.

12. The method of claim 1, wherein the predetermined threshold corresponds to a maximum force expected during a surgical procedure involving the MIS port.

13. A system for use during minimally invasive surgery, the system comprising:

a robotic arm;

a sensor;

at least one processor; and a memory storing instructions for execution by the at least one processor that, when executed, cause the at least one processor to:

determine, based on a surgical plan for a patient, a pose for a minimally invasive surgery (MIS) port;

cause the robotic arm holding the MIS port to manipulate the MIS port into the pose;

receive, from the sensor, information about a force exerted on the robotic arm via the MIS port;

maintain the MIS port in the pose when the force is lower than a predetermined threshold; and generate an alert when the force exceeds the predetermined threshold.

14. The system of claim 13, wherein the robotic arm or the MIS port comprises the sensor.

15. The system of claim 13, wherein the memory stores additional instructions for execution by the at least one processor that, when executed, further cause the at least one processor to:

move the MIS port to a new pose different than the pose.

16. The system of claim 13, wherein the alert comprises at least one of a visual alert, an audible alert, or a tactile alert.

17. The system of claim 13, wherein the determining comprises calculating an insertion vector based on the surgical plan.

18. The system of claim 13, wherein the predetermined threshold is based on a characteristic of the robotic arm.

19. A system for providing robotic assistance during surgery, the system comprising:

a robotic arm;

at least one processor; and a memory storing instructions for execution by the at least one processor that, when executed, cause the at least one processor to:

calculate, based on a surgical plan for a patient, a pose for a surgical port;

register a robotic coordinate space corresponding to the robotic arm to a patient coordinate space corresponding to the patient;

cause the robotic arm holding the surgical port to manipulate the surgical port into the pose;

control the robotic arm to maintain the surgical port in the pose unless a force exerted on the surgical port exceeds a predetermined threshold; and generate, when the force exceeds the predetermined threshold, an alert.

20. The system of claim 19, wherein the surgical port is a minimally invasive surgery (MIS) port or an endoscopy port.

* * * * *